(12) United States Patent
Ma et al.

(10) Patent No.: US 11,657,509 B2
(45) Date of Patent: May 23, 2023

(54) METHOD FOR PRECISELY AND AUTOMATICALLY POSITIONING REFERENCE LINE FOR INTEGRATED IMAGES

(71) Applicant: SHANGHAI UNITED IMAGING HEALTHCARE CO., LTD., Shanghai (CN)

(72) Inventors: Qingzhen Ma, Shanghai (CN); Yanyan Wang, Shanghai (CN); Bin Ouyang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 13 days.

(21) Appl. No.: 17/145,422

(22) Filed: Jan. 11, 2021

(65) Prior Publication Data

US 2021/0133978 A1 May 6, 2021

Related U.S. Application Data

(63) Continuation of application No. 16/218,013, filed on Dec. 12, 2018, now Pat. No. 10,909,685, which is a
(Continued)

(51) Int. Cl.
*G06T 7/11* (2017.01)
*G06T 7/174* (2017.01)
(Continued)

(52) U.S. Cl.
CPC .............. *G06T 7/11* (2017.01); *A61B 6/5235* (2013.01); *G06T 7/0014* (2013.01); *G06T 7/174* (2017.01);
(Continued)

(58) Field of Classification Search
CPC ......... G06T 7/11; G06T 7/0014; G06T 7/174; G06T 7/33; G06T 2207/10081;
(Continued)

(56) References Cited

U.S. PATENT DOCUMENTS

| 2007/0083117 A1* | 4/2007 | Sakas | A61B 8/4254 |
| | | | 600/437 |
| 2012/0176406 A1* | 7/2012 | Elenbaas | A61B 6/032 |
| | | | 345/629 |

(Continued)

FOREIGN PATENT DOCUMENTS

| CN | 102525525 A | 7/2012 |
| CN | 105342701 A | 2/2016 |

OTHER PUBLICATIONS

International Search Report in PCT/CN2017/084007 dated Feb. 13, 2018, 7 pages.
(Continued)

*Primary Examiner* — Amara Abdi
(74) *Attorney, Agent, or Firm* — Metis IP LLC

(57) ABSTRACT

The present disclosure involves a reference line determination method and system. In a process of determining a reference line, a plurality of original images containing a first spatial position information are obtained. According to the plurality of original images, a composite image containing a second spatial position information is further determined. After a composition relationship between a plurality of original images was determined, a reference line is determined on the composite image according to the spatial position information.

18 Claims, 9 Drawing Sheets

Related U.S. Application Data continuation of application No. PCT/CN2017/084007, filed on May 11, 2017.

(51) Int. Cl.
　　*G06T 7/00*　　(2017.01)
　　*A61B 6/00*　　(2006.01)
　　*G06T 7/33*　　(2017.01)

(52) U.S. Cl.
　　CPC ............... *G06T 7/33* (2017.01); *A61B 6/501* (2013.01); *G06T 2207/10081* (2013.01); *G06T 2207/10088* (2013.01); *G06T 2207/10104* (2013.01); *G06T 2207/30012* (2013.01)

(58) Field of Classification Search
　　CPC . G06T 2207/10088; G06T 2207/10104; G06T 2207/30012; A61B 6/5235; A61B 6/501
　　See application file for complete search history.

(56) References Cited

U.S. PATENT DOCUMENTS

| | | | |
|---|---|---|---|
| 2013/0039550 A1* | 2/2013 | Blum | G06T 7/0014 382/128 |
| 2015/0221091 A1 | 8/2015 | Sugiyama et al. | |
| 2016/0055634 A1 | 2/2016 | Bystrov et al. | |

OTHER PUBLICATIONS

Written Opinion in PCT/CN2017/084007 dated Feb. 13, 2018, 8 pages.

\* cited by examiner

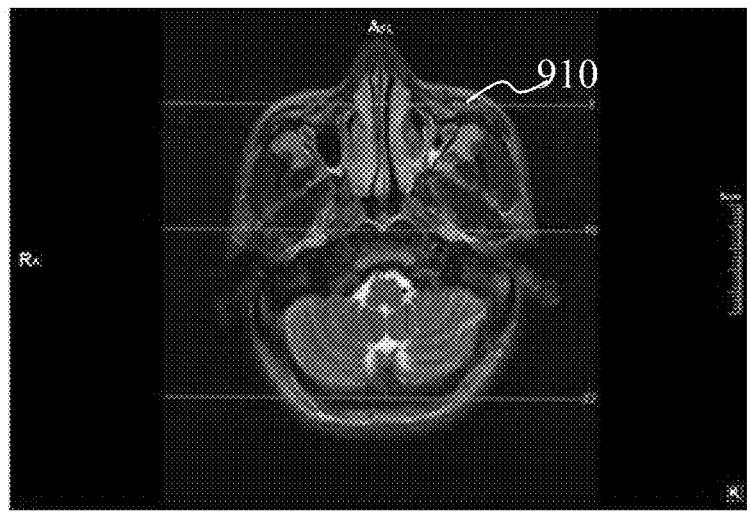
FIG. 9-A
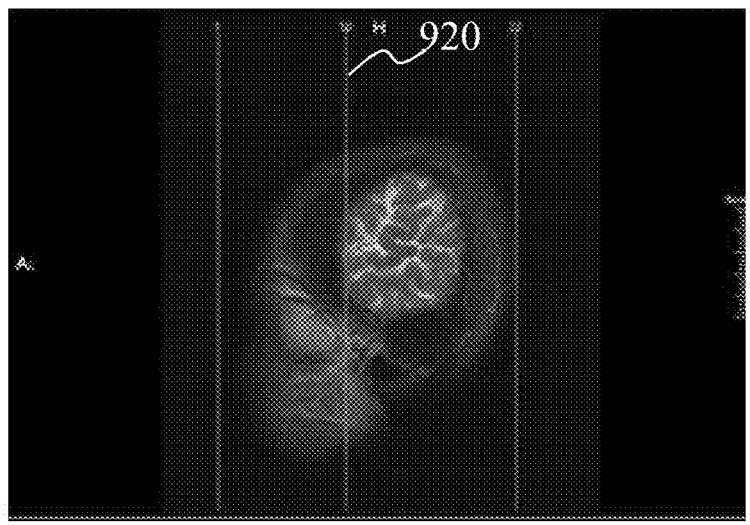
FIG. 9-B
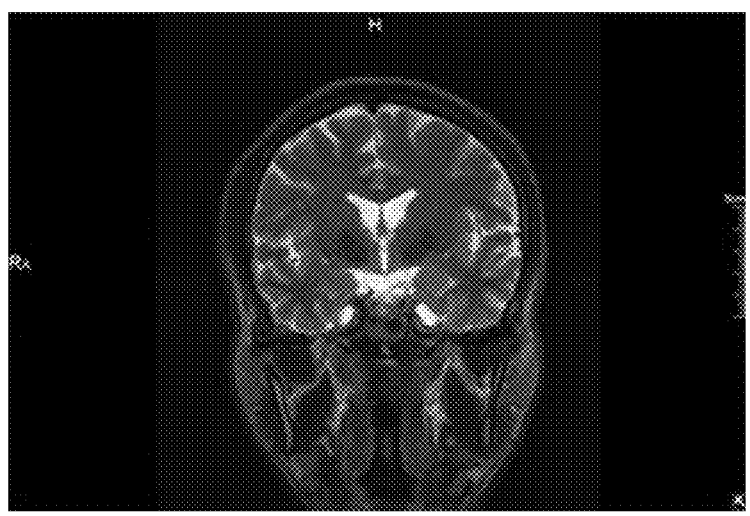
FIG. 9-C

METHOD FOR PRECISELY AND AUTOMATICALLY POSITIONING REFERENCE LINE FOR INTEGRATED IMAGES

CROSS-REFERENCE TO RELATED APPLICATIONS

This application is a continuation of U.S. patent application Ser. No. 16/218,013, filed on Dec. 12, 2018, which is a continuation of International Application No. PCT/CN2017/084007 filed on May 11, 2017, the entire contents of which are hereby incorporated by reference.

TECHNICAL FIELD

The present disclosure generally relates to the field of medical imaging, and more particularly, to a method and a device for precisely positioning a reference line.

BACKGROUND

In the medical imaging field, a reference line may have great significance for disease discovery, diagnosis, and treatment. For example, in a computed tomography (CT) image of human total vertebrae, a user (e.g., a doctor), can accurately obtain a size of lesion, a position of lesion and a position relationship between the lesion and important surrounding tissues based on a reference line. However, currently, display of the reference line in the medical image may have problems such as that the position is not accurate and no accurate adjustment can be done. For example, since the position may change during a composing process, the position of the reference line cannot be accurately displayed and the reference line may not be adjusted in some medical images (e.g., a vertebrae magnetic resonance imaging (MRI) image). Such problems may prevent a user (e.g., a doctor) from accurately, quickly and easily obtaining the position of the reference line, reducing the efficiency of disease diagnosis and treatment of a user (e.g., a doctor). Therefore there is a need for a new method or system for positioning the reference line, so that the position of the reference line can be accurately displayed and adjusted in the medical image. Such a method or a system of positioning the reference line will effectively increase the efficiency of disease diagnosis and treatment of a user (e.g., a doctor).

SUMMARY

According to an aspect of the present disclosure, a method for determining a reference line for MRI, CT and/or PET images is provided. The method may include one or more steps of following operations: obtaining at least two original images, the at least two original images corresponding to first spatial position information; determining a composite/integrated/fused image based on the at least two original images, the composite image corresponding to second spatial position information; determining a composition relationship between the at least two original images; and determining at least one reference line based on the composition relationship between the at least two original images, the first spatial position information, and the second spatial position information.

In some embodiments, the first spatial position information may include at least one of position information or direction information of the at least two original images; and the second spatial position information may include at least one of position information or direction information of the composite image.

In some embodiments, the determining a composition relationship between the at least two original images may include performing at least one of operations to the at least two original images including: translation; rotation; zoom; and cropping.

In some embodiments, the composition relationship between the at least two original images may include a registration matrix.

In some embodiments, the determining at least one reference line based on the composition relationship between the at least two original images may include: determining an intersection between the at least two original images and the composite image based on the first spatial position information and the second spatial position information; adjusting the intersection between the at least two original images and the composite image based on the composition relationship between the at least two original images; and determining the at least one reference line based on the adjusted intersection between the at least two original images and the composite image.

In some embodiments, the determining the intersection between the at least two original images and the composite image based on the first spatial position information and the second spatial position information may include: determining the intersection based on at least one plane of the at least two original images and a plane of the composite image.

In some embodiments, the determining at least one reference line may include:
determining a first reference line based on the first spatial position information and the second spatial position information; obtaining, based on an objective function, a transformation matrix by performing at least one of translation or rotation operation to the first reference line; and obtaining a second reference line by correcting the first reference line based on the transformation matrix.

According to an aspect of the present disclosure, a reference line determination system for MRI, CT and/or PET images is provided. The system may include a computer-readable storage medium configured to store a plurality of executable modules and a processor, the processor may be capable of executing the plurality of executable modules stored in the computer-readable storage medium. The plurality of executable modules may include: an image composition module and a reference line determination module. The image composition module may be configured to: obtain at least two original images, said at least two original images corresponding to first spatial position information; determine a composite image based on the at least two original images, the composite image corresponding to second spatial position information; and determine a composition relationship between the at least two original images; the reference line determination module may be configured to determine at least one reference line based on the composition relationship between the at least two original images, the first spatial position information, and the second spatial position information.

In some embodiments, the first spatial position information may include at least one of position information or direction information of the at least two original images; and the second spatial position information may include at least one of position information or direction information of the composite image.

In some embodiments, the determining a composition relationship between the at least two original images may include performing at least one of operations to the at least two original images including: translation; rotation; zoom; and cropping.

In some embodiments, the composition relationship between the at least two original images may include a registration matrix.

In some embodiments, the determining at least one reference line based on the composition relationship between the at least two original images may include:

determining an intersection between the at least two original images and the composite image based on the first spatial position information and the second spatial position information; adjusting the intersection between the at least two original images and the composite image based on the composition relationship between the at least two original images; and determining the at least one reference line based on the adjusted intersection between the at least two original images and the composite image.

In some embodiments, the determining the intersection between the at least two original images and the composite image based on the first spatial position information and the second spatial position information may include: determining the intersection based on at least one plane of the at least two original images and a plane of the composite image.

In some embodiments, the at least one reference line may include:
determining a first reference line based on the first spatial position information and the second spatial position information; obtaining, based on an objective function, a transformation matrix by performing at least one of translation or rotation operation to the first reference line; and obtaining a second reference line by correcting the first reference line based on the transformation matrix.

BRIEF DESCRIPTION OF THE DRAWINGS

The drawings described herein are used to provide a further understanding of the present disclosure, all of which form a part of this specification. It is to be expressly understood, however, that the exemplary embodiment(s) of this disclosure are for the purpose of illustration and description only and are not intended to limit the scope of the present disclosure. The same label in each drawing represents the same parts.

DETAILED DESCRIPTION

Figure 1:
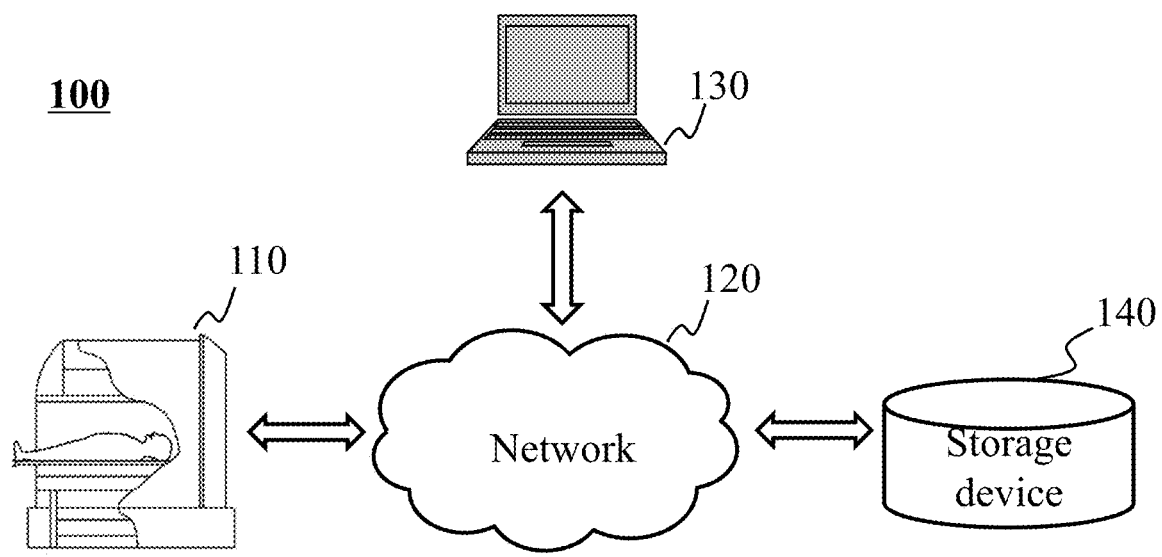
FIG. 1 illustrates a schematic diagram of a reference line positioning system according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. It is to be understood that these exemplary embodiments are given merely for the purpose of better understanding of the present invention by those skilled in the art, and are not intended to limit the scope of the invention in any way. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements.

Although the present disclosure makes various references to certain modules in the system according to some embodiments of the present disclosure, any number of different modules may be used and run on a client terminal and/or a server. The modules are illustrative only, and different aspects of the systems and methods may use different modules.

Flowcharts are used in the present disclosure to illustrate operations performed by the system according to some embodiments of the present disclosure. It should be understood that the preceding or following operations may not be necessarily performed exactly in order. Instead, various steps may be processed in reverse sequence and/or simultaneously. Moreover, other operations may also be added into these procedures, or one or more steps may be removed from these procedures.

FIG. 1 illustrates a schematic diagram of a reference line positioning system according to some embodiments of the present disclosure. A reference line may refer to an intersecting line between a first medical image and a second medical image displayed on the first medical image. The reference line may have important significance for various aspects such as description of lesion positions, determination of therapeutic plans, tumor intervention treatments, or the like, or a combination thereof.

A reference line positioning system 100 may include one or more imaging devices 110, one or more networks 120, one or more processing devices 130 and one or more storage devices 140, or the like, or a combination thereof.

The imaging device 110 may scan an object to be examined and obtain scanning data; the scanning data may be sent to the processing device 130 via the network 120 for further process, and the scanning data also may be stored in the storage device 140. The object to be examined may include human bodies, animals, etc. The imaging device 110 may include but not limited to a computed tomography (CT) device, a magnetic resonance imaging (MRI) device, or a positron emission computed tomography (PET) device.

The processing device 130 may process and analyze input data (for example, scanning data and scanning images obtained by the imaging device 110 and/or stored in the storage device 140) to generate processed results. For example, the processing device 130 may generate scanning images according to the scanning data. As another example, the processing device 130 may segment the scanning images to obtain a segmentation result. The scanning image may be two-dimensional image or three-dimensional image. The processing device 130 may include a processor and an input/output device (not shown in the figure). In some embodiments, the processor may be a server or a server group. A server group may be centralized, for example, a data center. A server group may also be distributed, for example, a distributed system. The processor may be a cloud server, a file server, a database server, a FTP server, an application server, a proxy server, a mail server, or the like, or a combination thereof. The server may be local, and may also be remote. In some embodiments, the server may access information stored in the storage device 140 (for example, a medical image stored in the storage device 140), information in the imaging device 110 (for example, a medical image photographed by the imaging device 110). In some embodiments, the input/output device may input data to the processor and may also receive data output by the processor, and may express the output data in a form of a numeral, a character, an image, sound, etc. In some embodiments, the input/output device may include but not limited to an input device, an output device, or the like, or a combination thereof. The input device may include but not limited to a character input device (for example, a keyboard), an optical reading device (for example, an optical mark reader, an optical character reader), a graphic input device (for example, a mouse, a joystick, a light pen), an image input device (for example, a camera, a scanner, a fax machine), an analog input device (for example, a language analog to digital conversion recognition system), or the like, or a combination thereof. The output device may include but not limited to a display device, a printing device, a plotter, an image output device, a voice output device, a magnetic recording system, or the like, or a combination thereof. In some embodiments, the processing device 130 may further include a storage device (not shown in the figure), and the storage device may store different information, for example, programs, data, etc. In some embodiments, intermediate data and/or a processed result (for example, a scanning image, an image segmentation result, etc.) generated by the processing device 130 may be stored in a storage device of the storage device 140 and/or the processing device 130, and may also be output by the input/output device.

In some embodiments, the data storage device 140 may refer to any device with a storage function in general. The data storage device 140 may mainly be used to store scanning data collected from the imaging device 110 and various data generated in the operation of the processing device 130. The storage device 140 or other storage devices in the system may refer to any media with read/write functions in general. The storage device 140 or other storage devices of the system may be internal or external to the system. The data storage device 140 may be local or remote. The data storage device 140 may include but is not limited to a hierarchical database, a networked database, a relational database, or the like, or any combination thereof. The storage device 140 may digitize information, and then store the digitized information in the storage device by an electrical method, a magnetic method, an optical method, or the like. The data storage device 140 may be used to store various types of information such as a system, software, a program, and data. The data storage device 140 may be a device that stores information by electrical energy method, e.g., various memories, a random access memory (RAM), a read-only memory (ROM), etc. The random access memory may include but is not limited to a decade counting tube, a selectron, a delay line memory, a Williams tube, a dynamic random access memory (DRAM), a static random access memory (SRAM), a thyristor random access memory (T-RAM), a zero-capacitor random access memory (Z-RAM), or the like, or any combination thereof. The read only memory may include but is not limited to a bubble memory, a twistor memory, a film memory, a plated wire memory, a magnetic-core memory, a drum memory, a CD-ROM, a hard disk, a tape, a NVRAM, a phase-change memory, a magneto-resistive random access memory, a ferroelectric random access memory, a nonvolatile SRAM, a flash memory, an electrically erasable programmable read-only memory (EEPROM), an erasable programmable read-only memory, a mask read only memory, a floating connected gate random access memory, a nano random access memory, a racetrack memory, a resistive random access memory, a programmable metallization unit, or the like, or any combination thereof. The storage device 140 may be a device that stores information by magnetic energy method, e.g., a hard disk, a soft disk, a tape, a magnetic core storage, a bubble memory, a U-Disk, a flash memory, etc. The storage device 140 may be a device that stores information by an optical method, e.g., a CD, a DVD, etc. The storage device 140 may be a device that stores information by the magneto-optical method, e.g., a magneto-optical disk, etc. Access modes of the storage device 140 may include random access mode, serial access mode, read-only access mode, or the like, or any combination thereof. The storage device 140 may be a non-permanent memory or a permanent memory. The storage devices described above is only examples. The database used in the reference line positioning system 100 are not intended to be limiting.

The network 120 may be a single network or a combination of multiple networks. The network 120 may include but is not limited to a local area network, a wide area network, a public network, a dedicated network, a wireless local area network, a virtual network, a metropolitan area network, a public switched telephone network, or the like, or any combination thereof. The network 120 may include a variety of network access points, such as wired or wireless access points, a base station, or network switching points. A data source may be connected to the network 120 through the access points. Information may be sent via the network.

It should be noted that the above description of the system is merely provided for the purpose of illustration, and not intended to limit the scope of the present disclosure. For persons having ordinary skills in the art, modules may be combined in various ways, or connected with other modules as sub-systems, and various modifications and transformations in form and detail may be conducted under the teaching of the present disclosure. However, those modifications and transformations may not depart from the spirit and scope of this disclosure. For example, the storage device 140 may be a cloud computing platform with data storage function including but not limited to a public cloud platform, a private cloud platform, a community cloud platform, a hybrid cloud platform, etc. All such transformations are within the protection scope of the present disclosure.

Figure 2:
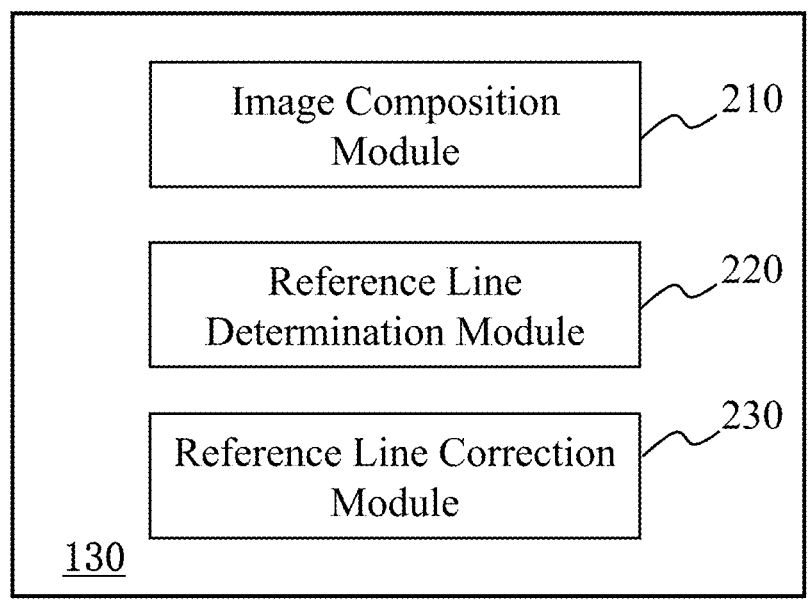
FIG. 2 illustrates a schematic diagram of a processing device 130 according to some embodiments of the present disclosure.

FIG. 2 illustrates a schematic diagram of a processing device 130 according to some embodiments of the present disclosure. The processing device 130 may include an image composition module 210, a reference line determination module 220, and a reference line correction module 230. The modules described in FIG. 2 may be implemented by a computer described in FIG. 7 via a CPU unit 720. The modules may be directly (and/or indirectly) connected. Apparently, the processing device 130 in FIG. 2 may only represent some embodiments of the present disclosure, for those of ordinary skill in the art, modification, addition or deletion may be made according to FIG. 2 without any creative works. For example, two modules therein may be combined into one module, alternatively, one module may be segmented into two or more modules.

In some embodiments, the image composition module 210 may generate one or more composite images based on original images. The image composition module 210 may obtain the original images from the imaging device 110. The obtained original images may include but not limited to one or more medical images (for example, a CT image, an MRI image, a PET image, etc.). The original images may be two-dimensional images or three-dimensional images. The original images may include but not limited to raw images and/or processed images. The raw images may refer to images directly obtained according to the scanning data (for example, medical images). The processed images may refer to images obtained by processing the raw images. The processing of the raw images may include but not limited to image enhancement, image reconstruction, three-dimensional reconstruction, image filtering, image coding (for example, compression coding), image format conversion, image rendering, image zoom, or the like, or a combination thereof.

The number of the obtained original images may be two or more. In some embodiments, several original images may be generated by scanning the same object to be examined (for example, a human body, a part of the human body, etc.) from different angles. In some embodiments, the imaging device 110 may generate a plurality of image segments based on a plurality of different angles. Each image segment may include at least one original image, and the original image may have related or similar spatial position information. For example, the imaging device 110 may photograph the human total vertebrae from three different angles to obtain three image segments: an image segment A (such as, a cervical vertebra image segment), an image segment B (such as, a thoracic vertebra image segment), and an image segment C (such as, a lumbar vertebra image segment). The number of original images contained in the image segment A, the image segment B, and the image segment C may be the same or different.

The original images may be two-dimensional images or three-dimensional images. For example, the original images may be two-dimensional images showing the human total vertebrae. As another example, the original images may be three-dimensional images showing a human liver. In some embodiments, the original images may be generated based on original images with a same modality or original images with different modalities. For example, the original images may be generated based on medical images (e.g., an MRI image, a CT image, a PET image, etc.) with different modalities. The medical images with a same modality (medical images with different modalities) may correspond to a same object to be examined or different objects to be examined and/or different parts of the same object to be examined. For example, a composite image of the human total vertebrae may be composite based on an MRI image (e.g., a cervical vertebra image segment) and a CT image (e.g., a lumbar vertebra image segment).

In some embodiments, the reference line determination module 220 may determine a reference line. The reference line may be used to display a positional relationship between another image and current reference image on a reference image. The reference line may include elements such as one or more straight lines, a line segment, a curved line, a point, etc. The reference line may include any number of pixels. In some embodiments, the reference line may be commonly expressed using a straight line, a dashed line, a line segment, etc., on the reference image. The reference image may be a composite image or an original image. For example, during a head CT scan, the imaging device 110 may generate an axial image, a sagittal image, or a coronal image of a cranium. The reference line determination module 220 may determine and/or display one or more reference lines in the axial image, and the reference line may be used to show a positional relationship between the coronal image and the axial image (as shown in FIG. 9A). The axial image may represent an image transecting the object to be examined into upper and lower parts when the object to be examined (for example, a human body) stands on the ground, the image being perpendicular to the sagittal image and the coronal image. The sagittal image may represent an image slitting the object to be examined into left and right parts based on a front-rear direction of the object to be examined when the object to be examined (for example, a human body) stands on the ground. The coronal image may represent an image cropping the object to be examined into front and rear parts based on a left-right direction of the object to be examined when the object to be examined (for example, a human body) stands on the ground.

In some embodiments, the reference line determination module 220 may determine and display a plurality of reference lines between the original image and the current composite image on the composite image. For example, on the composite image of a human total vertebrae, the reference line determination module 220 may display five reference lines. The reference lines may show a positional relationship between the composite image of the human total vertebrae and five axial images (e.g., five lumbar vertebra axial images). A user (e.g., a doctor) may analyze an accurate position of an axial image of a certain lumbar vertebra on the human total vertebrae (e.g., the axial image of a fracture lumbar vertebra may belong to the second lumbar vertebra) to perform disease diagnosis and subsequent treatment.

In some embodiments, the reference line correction module 230 may correct a position of the reference line. In some embodiments, the reference line determination module 220 may display a reference line corresponding to an original image on the composite image. The positions of the reference lines corresponding to the original images may be inaccurate since a position relationship between the original images may change during a generation process of the composite image. For example, a position of the reference line displayed on the composite image of the human total vertebrae may be beyond a upper and lower range of a vertebrae (for example, the position of the reference line is higher than altlas), or an angle of the reference line and vertebrae may not correspond to an actual scanning angle (for example, a direction of the reference line of the vertebral axial image is parallel or substantially parallel to a vertebral direction), etc. The reference line correction module 230 may manually or automatically correct the reference line position.

In some embodiments, a user (e.g., a doctor) may input a correction command via an input/output component 760 or an input/output (I/O) unit 850. The correction command may include translation, rotation, addition, deletion of the reference line, or the like, or a combination thereof. The reference line correction module 230 may obtain the correction command and correct the reference line accordingly. In some embodiments, a user (e.g., a doctor) may preset reference line correction rules (for example, parallel spacing of the reference line is greater than 5 mm or other threshold, or the specific thickness of the reference line, or the specific length of the reference line, etc.) based on the network 120, a computer 700 or a mobile device 800. According to the reference line correction rules, the reference line correction module 230 may automatically correct the reference line accordingly.

Figure 3:
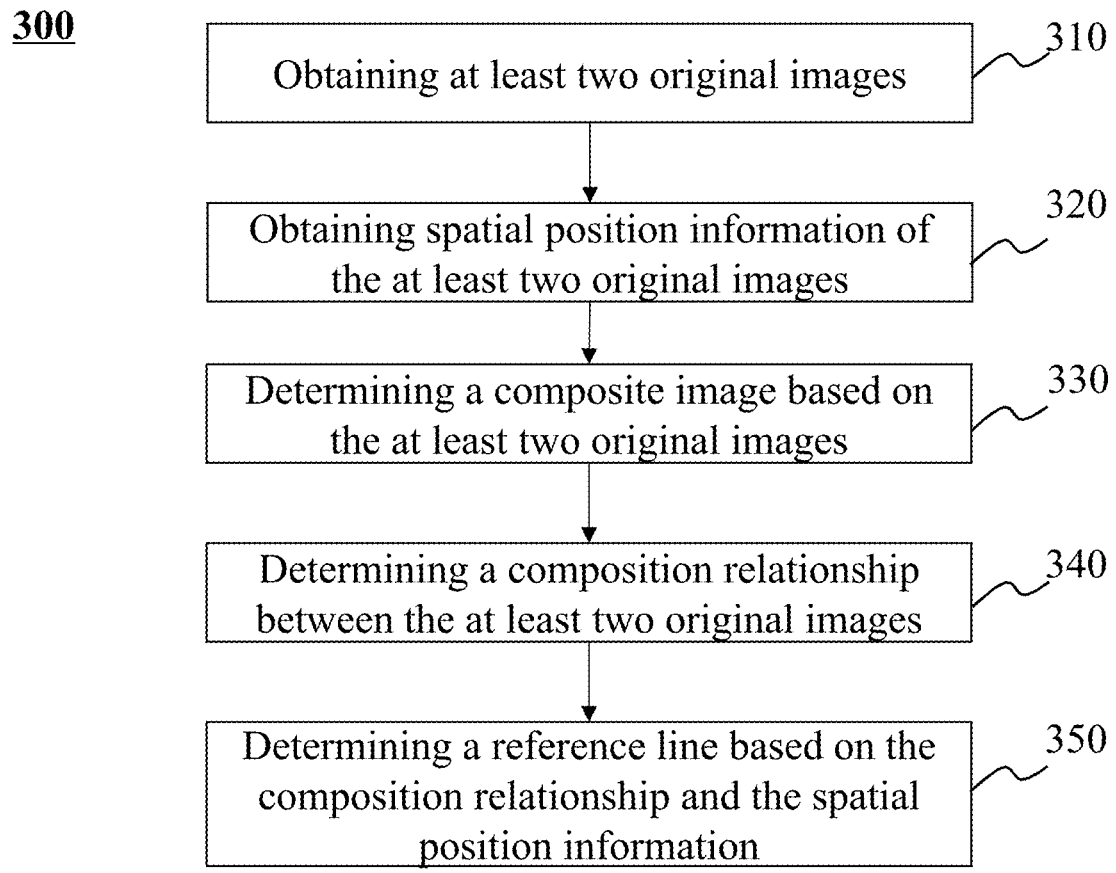
FIG. 3 illustrates a flowchart of an exemplary process for positioning a reference line according to some embodiments of the present disclosure.

FIG. 3 illustrates a flowchart of an exemplary process for positioning a reference line according to some embodiments of the present disclosure. A process 300 may be implemented by one or more hardware, software, firmware, or the like, or a combination thereof. In some embodiments, the process 300 may be implemented by one or more processing devices (for example, the processing device 130 shown in FIG. 1) and/or a computing device (for example, a computer shown in FIGS. 7 and 8) for operating the image composition module 210.

At 310, the image composition module 210 may obtain at least two original images. The original images may be scanning images. The scanning images may include but not limited to CT images, MRI images, or PET images. The scanning images may be two-dimensional images or three-dimensional images. The scanning image may include but not limited to raw images and/or processed images. The raw images may refer to images obtained directly according to the scanning data. The processing images may refer to images obtained by processing the raw images. The processing of the raw images may include but not limited to image enhancement, image reconstruction, three-dimensional reconstruction, image filtering, image coding (for example, compression coding), image format conversion, image rendering, image zoom, or the like, or a combination thereof.

The image enhancement may mean increased contrast of whole or partial regions of images. For example, in a human vertebral MRI image, contrast of vertebrae and surrounding nerves or soft tissues may be enhanced, so as to allow an imaging technician or a doctor to quickly and easily identify boundaries of vertebral edges. As another example, for a craniocerebral MRI image, certain lesions (epileptic focus) or brain tissues of important functional areas may be added to facilitate the doctor to determine a surgically cropping range, thereby reducing damages to normal brain tissues, particularly, brain tissues of the important functional areas, while resecting the lesions within the largest range. In some embodiments, the image enhancement may include contrast enhancement, noise removal, background removal, edge sharpening, filtering, wavelet transform, or the like, or a combination thereof.

Image reconstruction may represent generating images in any planar according to existing MRI scanning images. Three-dimensional reconstruction may represent obtaining hepatic three-dimensional images according to hepatic two-dimensional scanning images. For example, the image composition module 210 may allow a vertebral MRI image to be converted into a visualization toolkit image format (VTI format) from a digital imaging and communications in medicine (DICOM) format.

Image encoding may also refer to image compression, representing expressing image or information contained in the image using a small number of bits when certain image quality (for example, SNR) is achieved. Image rendering may represent converting high dimensional information into low dimensional information, for example, converting three-dimensional information into two-dimensional information.

In some embodiments, the image composition module 210 may obtain scanning data from the imaging device 110, and reconstruct the raw images based on the scanning data. Methods for MRI reconstruction by the image composition module 210 may include an MRI reconstruction method based on K-space filling or an MRI reconstruction method based on image domain. The MRI reconstruction method based on K-space filling may include a half-Fourier imaging method, a SMASH imaging method, or an AUTO-SMASH imaging method, etc. The MRI reconstruction method based on image domain may perform MRI image reconstruction by using some priori information on an MRI image, the method may decrease data scanning time, thereby accelerating a process of MRI imaging. The MRI reconstruction method based on the image domain may reconstruct images according to different sensitivity information between coils, or may reconstruct images according to sparsity of the MRI image (for example, MRI image reconstruction may be performed by using a compression sensing method.)

At 320, the image composition module 210 may obtain spatial position information of the original images. The spatial position information may include three-dimensional coordinate information, two-dimensional coordinate information of the original images, spatial position information in a specific image format, etc. The spatial position information of the original images may be obtained from image data in any image formats. The image formats may include but not limited to a DICOM format, a VTI format, etc. The image data may include one or more logic levels. The image data may include a file header and a data set group in a physical structure. The file header may include a preamble (for example, 128 bytes) and a prefix (for example, 4 bytes). The preamble may have a fixed structure or not. For example, in some embodiments, when there is no content, bytes may be set to OOH and the prefix may be a DICOM character string, so as to identify a DICOM file. The data set may have stored all necessary information for operating the DICOM file, and may include a plurality of data elements. Each data element may include four fields of Tag, Vale Representation, Value Length, and Value Field, and have stored a formatting rule and content of the element information.

The spatial position information of the original images obtained by the image composition module 210 may include position information of the original images (for example, image position (patient) in DICOM), direction information of the original images (for example, image orientation (patient) in DICOM), and other information related to spatial positions. The position information of the original images may include coordinate information related to the original images (for example, coordinates of pixels in the first row and the first column of the original images (for example, upper left corner)). The coordinate information may include one or more coordinates in any coordinate system. In some embodiments, the position information of the original images may include one or more coordinates in a specific coordinate system. For example, the spatial position information of the original images may be represented as O1 (x1, y1, z1).

The direction information of the original images may include any information related to directions in the original images. For example, the direction information of the original images may include direction information (one or more directions, vectors representing directions, triangle function values corresponding to one or more directions, etc.) corresponding to one or more parts (for example, pixels in the first row and/or pixels in the first column) of the original images. For example, the direction information of the original images may include a direction vector in the first row, and a direction vector in the first column in the original images. As another example, the direction information of the original images may be represented as a normal vector of the original images. In some embodiments, the normal vector may be a cross-product of the direction vector in the first row and the direction vector in the first column.

In some embodiments, the original image may be represented as Equation (1):

$$(x-x1)nx+(y-y1)ny+(z-z1)nz=0 \qquad (1)$$

wherein, (x1, y1, z1) is the position information of the original images, and (nx, ny, nz) is the direction information of the original images (e.g., the normal vector).

At 330, the image composition module 210 may determine a composite image based on the at least two original images. The original images may include a first original image, a second original image, etc. The image composition module 210 may determine a composite image by performing transformation such as translation, rotation, scale up, shear, etc. on the original images. For example, the image composition module 210 may set any one of the at least two original images as a fixed reference image (e.g., the first original image), and translation and/or rotation transformation may be performed on the other original images according to the fixed reference image.

At 330, the image composition module 210 may obtain spatial position information of the composite image. The spatial position information may include three-dimensional coordinate information of the composite image, two-dimensional coordinate information of the composite image, spatial position information in a specific image format, etc.

The spatial position information obtained by the image composition module 210 may include position information of the composite image (for example, image position patient in DICOM), direction information of the composite image (for example, image orientation patient in DICOM), etc. The position information of the composite image may include coordinate information related to the composite image (for example, coordinates of pixels in the first row and the first column (the upper left corner) in the composite image). The coordinate information may include one or more coordinates in any coordinate system. In some embodiments, the position information of the composite image may include one or more coordinates in specific coordinate systems. For example, the spatial position information of the original images may be represented as O2 (x2, y2, z2).

The direction information of the composite image may include any information related to directions in the composite image. For example, the direction information of the composite image may include direction information (one or more directions, vectors representing directions, triangle function values corresponding to one or more directions, etc.) corresponding to one or more parts (for example, pixels in the first row and/or pixels in the first column) of the composite image. For example, the direction information of the composite image may include a direction vector in the first row and a direction vector in the first column in the composite image. As another example, the direction information of the composite image may be represented as the normal vector of the original images. In some embodiments, the normal vector may be a cross-product of the direction vector in the first row and the direction vector in the first column.

In some embodiments, the spatial position information of the composite image may be represented as Equation (2):

$$(x-x2)Nx+(y-y2)Ny+(z-z2)Nz=0 \qquad (2)$$

wherein, (x2, y2, z2) is the position information of the composite image, and (Nx, Ny, Nz) is the direction information of the composite image.

In some embodiments, the image composition module 210 may determine the composite image based on a composition algorithm. The composition algorithm may include an area-based composition algorithm, and a feature-based composition algorithm. The area-based composition algorithm may calculate differences in gray values of the original images using the least squares method, determine a similarity of overlapping areas between the original images based on the differences in the gray values, determine a range and a position of the overlapping areas between the original images based on the similarity, and finally, generate the composite image. The feature-based composition algorithm may include feature extraction and feature alignment. Feature alignment algorithms may include algorithms such as cross correlation, distance transformation, dynamic programming, structure matching, chain code correlation, etc.

At 340, the reference line determination module 220 may determine a composition relationship between the original images (for example, a first original image and a second original image). The composition relationship may be used to represent position relationships between the original images in a process of determining a composite image. The position relationships between the original images may include translation, rotation, scale change, shear, or the like, or a combination thereof. In some embodiments, during CT scanning of a human total vertebrae, the image composition module 210 may select a first original image as a fixed reference image, and compose images based on a composition algorithm. For example, the image composition module 210 may adjust a second original image with respect to a position of the fixed reference image (the first original image), and may also adjust a size, a direction, etc. of the second original image. During the transformation, the reference line determination module 220 may determine and/or store the position relationship between the original images (e.g., between the first original image and the second original image). The position relationship between the original images may be represented as a registration matrix. In some embodiments, the registration matrix may be a 4*4 matrix:

$$\begin{pmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{pmatrix},$$

wherein, first three rows of the registration matrix may represent affine transformation, including rotation, translation, and shear. Fourth row of the matrix may represent projective transformation.

At 350, the reference line determination module 220 may determine a reference line based on spatial relative position information and the composition relationship between the original images. In some embodiments, the reference line determination module 220 may determine a reference line directly based on spatial position information of the first composite image, spatial position information of the second composite image and composition relationship between the second composite image and the first composite image. For example, the reference line determination module 220 may directly determine a reference line on the first composite image based on the position information of the first composite image, the position information of the second composite image and the registration matrix (e.g., a 4*4 matrix) between the first original image and the second original image, and the reference line may correspond to the second composite image.

In some embodiments, the reference line determination module 220 may determine an initial reference line on the composite image based on the spatial position information of the original images and the spatial position information of the composite image; and determine a corrected reference line based on the initial reference line and the composition relationship. For example, on a CT image of a human total vertebrae, the reference line determination module 220 may determine an initial reference line based on a three-dimensional coordinate (e.g., three-dimensional coordinates of upper-left pixels) of the original images and spatial position information of a composite image; and further determine a position of the corrected reference line or display the corrected reference line based on the initial reference line and a registration matrix between the original images.

Figure 4:
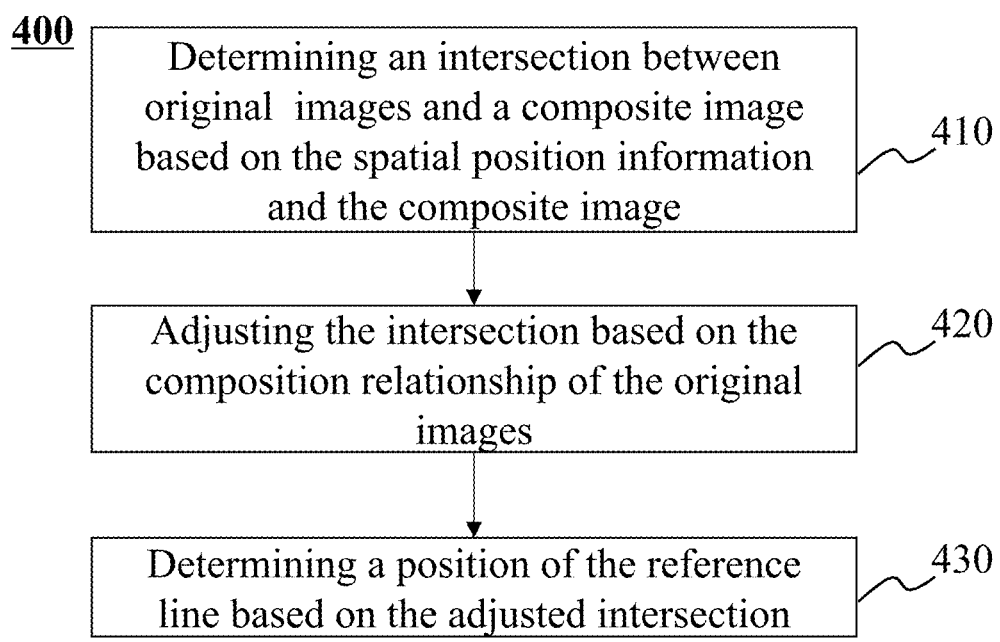
FIG. 4 illustrates a flowchart of an exemplary process for determining a reference line based on a spatial position relationship and a composition relationship according to some embodiments of the present disclosure.

FIG. 4 illustrates a flowchart of an exemplary process for determining a reference line based on a spatial position relationship and a composition relationship according to some embodiments of the present disclosure. A process 400 may be implemented by one or more hardware, software, firmware, or the like, or a combination thereof. In some embodiments, the process 400 may be implemented by one or more processing devices (for example, the processing device 130 shown in FIG. 1) and/or a computing device (for example, a computer shown in FIGS. 7 and 8) for operating the image composition module 210.

At 410, the reference line determination module 220 may determine an intersection between the original image and the composite image. In some embodiments, the reference line determination module 220 may determine an intersection between the original image and the composite image based on spatial information of original image and spatial information of the composite image. The intersection between the original image and the composite image may be determined based on a plane of the composite image and the original image located or an equation of a plane thereof. In some embodiments, the reference line determination module 220 may determine a plane of the composite image or an equation of a plane thereof based on the spatial position information of the composite image (e.g., position information or direction information). The reference line determination module 220 may determine a plane of the original image or an equation of a plane thereof based on the spatial position information of the original image (e.g., position information or direction information). The equation of the plane of the composite image and/or the equation of the plane of the original image may include an intercept equation of a plane, a point normal equation of a plane, a general equation of a plane, a normal equation of a plane, or the like, or a combination thereof. For example, the reference line determination module 220 may obtain a pixel coordinate O1 (x1, y1, z1) based on the position information of the original image; and may obtain a normal vector (dx, dy, dz) of the original image based on the direction information of the original image. The reference line determination module 220 may also determine a point normal form plane equation based on the pixel coordinate O1 (x1, y1, z1) and the normal vector (dx, dy, dz).

In some embodiments, the intersection between the original image and the composite image may be determined based on face to face intersecting or a solution of two equations of planes. In some embodiments, the reference line correction module 230 may calculate a solution between the equation of the plane of the original image and the equation of the plane of the composite image, to determine the intersection between the original image and the composite image. In some embodiments, if there is no intersection between the original image and the composite image, the reference line correction module 230 may determine that the original image and the composite image are in parallel or process in other ways.

At 420, the reference line correction module 230 may adjust the intersection based on the composition relationship between the original images. In some embodiments, the reference line correction module 230 may adjust the intersection based on a registration relationship between the original images, and obtain an adjusted intersection. For example, the composition relationship between the first original image (a fixed reference image) and the second original image may be represented by a registration matrix (e.g., a 4*4 matrix) or may be stored in the storage device 140. The reference line correction module 230 may calculate a solution of a plane equation corresponding to the second original image and a plane equation corresponding to the first composite image, and further determine an intersection between the first original image and the second image. The intersection of the second original image may be adjusted on the first composite image based on the registration matrix (e.g., a 4*4 matrix). As another example, if the second original image translates five units towards the positive direction of a X axis with respect to the first original image (a fixed reference image) during the composing process, the reference line correction module 230 may, after determining an intersection between the composite image and the second original image, translate the intersection five units towards the negative direction composite image and obtain an adjusted intersection.

At 430, the reference line correction module 230 may determine a position of the reference line based on the adjusted intersection. In some embodiments, the intersections between the original image and the composite image may be more than one (for example, two). For example, the reference line correction module 230 may determine two intersections on two relatively parallel sides in a plane of the composite image, based on four sides in a plane of the original image and a plane of the composite image. The two intersections may be adjusted in 420, and further two adjusted intersections may be determined. Based on the two adjusted intersections of the composite image, the reference line correction module 230 may connect the two adjusted intersections, and generate a line segment. The line segment may be used as a reference line of the original image corresponding to the composite image.

In some embodiments, the intersections between the original image and the composite image may be two or more. For example, the reference line correction module 230 may determine 100 intersections on the composite image based on the plane equation of the original image and the plane equation of the composite image; after the 100 intersections have been adjusted, the reference line correction module 230 may retain part of the adjusted intersections on the composite image, or may delete part of the adjusted intersections. The deletion of part of the adjusted intersections may be based on a length, a region, etc., of the reference line displayed on the composite image. For example, if the length of the reference line is set to 5 cm by the system 100, the reference line correction module 230 may delete intersections within 5 cm, and determine a line segment as a reference line based on the retained intersections.

Figure 5:
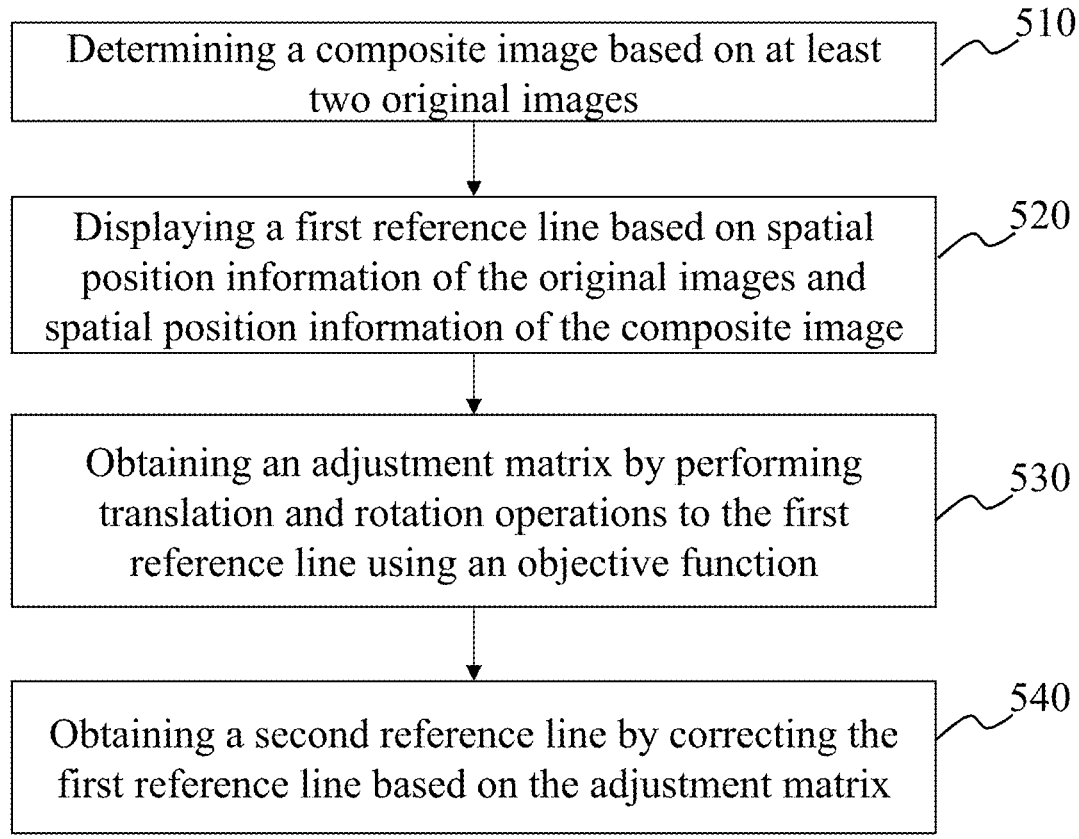
FIG. 5 illustrates a flowchart of an exemplary process for correcting a reference line according to some embodiments of the present disclosure.

FIG. 5 illustrates a flowchart of an exemplary process for correcting a reference line according to some embodiments of the present disclosure. A process 500 may be implemented by one or more hardware, software, firmware, or the like, or a combination thereof. In some embodiments, the process 500 may be implemented by one or more processing devices (for example, the processing device 130 shown in FIG. 1) and/or a computing device (for example, a computer shown in FIGS. 7 and 8) for operating the image composition module 210.

At 510, the reference line correction module 230 may obtain at least two original images, and determine a composite image based on the at least two original images. The original images may be scanning images. The scanning images may include but not limited to CT images, MRI images or PET images. The scanning images may be two-dimensional images or three-dimensional images.

In some embodiments, the original images may include a plurality of image segments, each image segment may include at least one original image, and the original image may have the same or similar spatial position information. For example, the imaging device 110 may photograph the human total vertebrae based on three different angles and obtain three image segments: an image segment A (e.g., a cervical vertebra image segment), an image segment B (e.g., a thoracic vertebra image segment), and an image segment C (e.g., a lumbar vertebra image segment); and the image segment A, the image segment B and the image segment C may include 50, 40, and 55 original images, respectively.

In the process of generating the composite image, the image composition module 210 may determine a composition relationship using the image segment as a unit. For example, the CT image of the human total vertebrae may include three image segments: an image segment A, an image segment B and an image segment C; each image segment may include at least one original image, and the original image in the same image segment may have similar spatial position information, for example, the same plane direction or the same scanning mode (for example, the image segment A may be axial scanning, the image segment B may be sagittal scanning, or the image segment C may be coronal scanning); and in the composing process, the image composition module 210 may take the image segment A as a fixed reference image segment, and perform transformation such as translation, rotation, scale change, or shear on the image segment B or the image segment C, so as to obtain the composite image.

At 520, the reference line determination module 220 may determine and/or display a first reference line, based on a spatial position relationship of the original image and a spatial position relationship of the composite image. The first reference line may be an initial reference line, or may be a reference line adjusted based on the initial reference line and the composition relationship. In some embodiments, the reference line determination module 220 may directly determine a plane of the original image and a plane of the composite image based on the spatial position relationship of the original image and the spatial position relationship of the composite image, and determine an intersection between the two planes; the reference line determination module 220 may directly determine a line segment or a straight line based on the intersection, as the first reference line. For example, the reference line determination module 220 may determine a first reference line of an axial image of the fourth thoracic vertebra on the composite image of the human total vertebrae based on a plane of the axial image of the fourth thoracic vertebra and a plane of the composite image of the human total vertebrae, and the first reference line may pass the fourth thoracic vertebra on the composite image and be perpendicular to or substantially perpendicular to a human total vertebrae direction.

In some embodiments, the reference line determination module 220 may determine the plane of the original image and the plane of the composite image based on the spatial position relationship of the original image and the spatial position relationship of the composite image, and may determine an intersection between the determined planes and an initial reference line. The reference line determination module 220 may adjust a position of the initial reference line based on the composition relationship, and determine a position of the first reference line based on the adjusted initial reference line. For example, the reference line determination module 220 may adjust an initial reference line between the plane of the original image and the plane of the composite image based on a registration matrix (e.g., a 4*4 matrix); and may determine a first reference line based on the adjusted initial reference line.

At 530, the reference line correction module 230 may perform a correction operation to the first reference line based on an objective function, and obtain an adjustment matrix. The correction operation may include translation, rotation, scale change, shear, or the like, or a combination thereof. The correction may be performed on the first reference line. The transformation matrix may represent the correction operation of the first reference line. In some embodiments, the transformation matrix may be stored in the storage device 140 or the network 120. In some embodiments, in the three dimensional space, if the plane of the original image and the plane of the composite image may be expressed in homogeneous coordinates, the transformation matrix corresponding to the first reference line may include a 4*4 matrix:

$$\begin{pmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{pmatrix},$$

wherein, $$\begin{pmatrix} a_{11} & a_{12} & a_{13} & a_{14} \\ a_{21} & a_{22} & a_{23} & a_{24} \\ a_{31} & a_{32} & a_{33} & a_{34} \end{pmatrix}$$

may represent rotation, translation, or shear, and ($a_{41}$ $a_{42}$ $a_{43}$ $a_{44}$) may represent projective transformation.

At 540, the reference line correction module 230 may correct the first reference line based on the transformation matrix, and obtain a second reference line. In some embodiments, the reference line correction module 230 may determine a second reference line based on a transformation matrix, and the second reference line may be represented as Equation (3):

$$Y'=mY \tag{3}$$

wherein, Y' represents a second reference line; Y represents a first reference line without a correction operation; and m represents a transformation matrix in the three dimensional space, and m may be a 4*4 matrix.

In some embodiments, the second reference line may be displayed on the computer 700 or on the mobile device 800 via the network 120. Take the MRI scanning image of the human total vertebrae as an example, the processing device 130 may display the composite image and the second reference line on the mobile device 800 (e.g., a smartphone) of a user (e.g., a doctor) via the network 120, allowing the user to perform remote diagnosis and treatment; taking the human head CT scanning image as another example, the processing device 130 may send the composite image and the second reference line to a cloud; a user (e.g., a doctor) may obtain the composite image and the second reference line via the cloud and display the composite image and the second reference line on the smartphone, so that the user can remotely receive imaging information.

Figure 6:
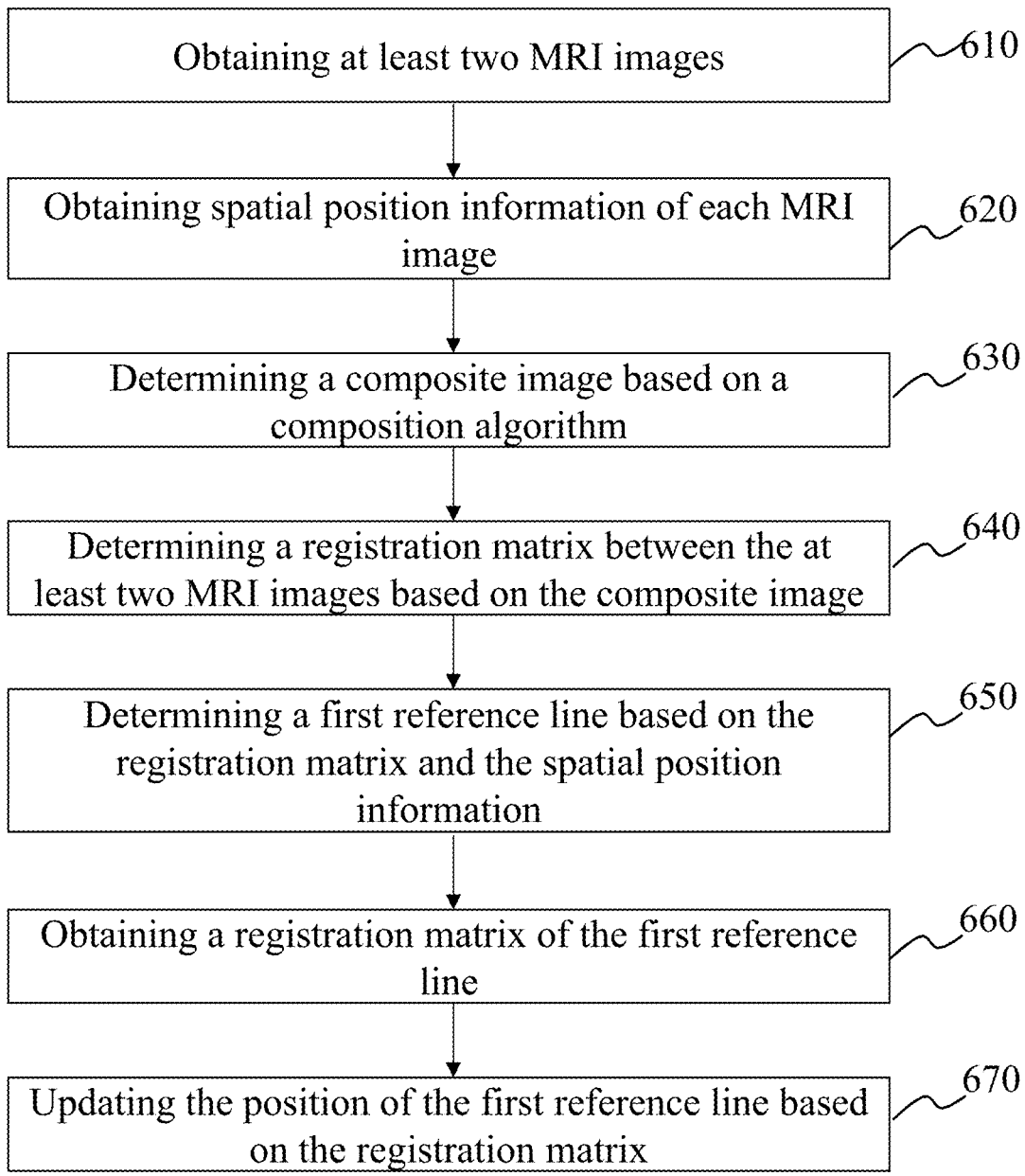
FIG. 6 illustrates a schematic diagram of adjusting a reference line according to some embodiments of the present disclosure.

FIG. 6 illustrates a schematic diagram of adjusting a reference line according to some embodiments of the present disclosure. A process 600 may be implemented by one or more hardware, software, firmware, etc., or the combination thereof. In some embodiments, the process 600 may be implemented by one or more processing devices (for example, the processing device 130 shown in FIG. 1) and/or a computing device (for example, a computer shown in FIGS. 7 and 8) operating the image composition module 210.

At 610, the processing device 130 may obtain at least two MRI images (for example, a first MRI image, a second MRI image, etc.). The at least two MRI images may involve any scanned object. For example, the at least two MRI images may include an MRI scanning image of a human total vertebrae, an MRI scanning image of a head, etc. In some embodiments, the MRI scanning image of the human total vertebrae may include at least three image segments: a cervical vertebra image segment, a thoracic vertebra image segment, and a lumbar vertebra image segment. The image segments may include one or more original MRI images, and the MRI image within each image segment may have the same or similar composition relationship in a subsequent composing process. In some embodiments, the at least two MRI images may be generated at different time. For example, the at least two MRI images may include a vertebrae MRI image before surgery and a vertebrae MRI image after the surgery.

At 620, the processing device 130 may obtain spatial position information of each MRI image. The spatial position information may include three-dimensional coordinate information, two-dimensional coordinate information of the original images, or spatial position information in a specific image format. In some embodiments, spatial position information of the composite image obtained by the image composition module 210 may include position information (for example, image position patient in a DICOM format), direction information (for example, image orientation patient in a DICOM format), etc. In some embodiments, the processing device 130 may obtain spatial position information of different image segments. For example, on the MRI scanning image of the human total vertebrae, the processing device 130 may obtain spatial position information of a cervical vertebra image segment, a thoracic vertebra image segment, and a lumbar vertebra image segment, so as to determine position changes of each segment, after composite, with respect to a certain fixed reference segment.

At 630, the processing device 130 may determine a composite image based on a composition algorithm. The composition algorithm may include a composition algorithm based on areas and a composition algorithm based on features. The composition algorithm based on areas may calculate, based on gray values of the original images, a difference of the gray values using the least squares method; judge similarity of overlapping areas between the original images based on the difference of the gray values; and determine a range and a position of the overlapping areas between the original images based on the similarity, finally, generating a composite image. The composition algorithm based on features may include feature extraction and feature alignment. Feature alignment algorithms may include algorithms e.g. a cross correlation algorithm, a transformation algorithm, a dynamic programming algorithm, a structure matching algorithm, a chain code correlation algorithm, etc. For example, using the composition algorithm based on areas, the processing device 130 may generate a composite image based on at least two MRI images or a plurality of image segments. The composite image may be a coronal image of the human total vertebrae.

At 640, the processing device 130 may determine a registration matrix between the MRI images based on the composite image. In some embodiments, the processing device 130 may take a certain MRI image or image segment (e.g., a cervical vertebra image segment) as a fixed reference, and then determine a composition relationship of other MRI images or image segments (e.g., a thoracic vertebra image segment or a lumbar vertebra image segment). For example, the processing device 130 may take a first MRI image as a fixed reference. The composition relationship may be represented as a registration matrix. In some embodiments, in a composing process of three-dimensional space, the processing device 130 may determine a plane of each MRI image before combination and a plane of that after combination, and determine a partial registration matrix based on position relationships of each MRI image with respect to the fixed reference image. In some embodiments, in three-dimensional space, if a plane of the MRI image is represented by homogeneous coordinates, after a composition operation, a corresponding registration matrix may be represented as a 4*4 matrix, e.g. Equation (4):

$$P'=nP \tag{4}$$

wherein, P' represents an MRI image after combination; P represents an MRI image without a composition; and n represents a registration matrix in a three-dimensional space, and n is a 4*4 matrix.

At 650, the processing device 130 may determine a first reference line based on the registration matrix and a spatial position relationship. The processing device 130 may determine a first reference line of an MRI image on a composite image of the total vertebrae. In some embodiments, the processing device 130 may determine an equation of a plane of an MRI image and an equation of a plane of a total vertebrae composite image; and based on the equation of the plane of the MRI image and the equation of the plane of the total vertebrae composite image, the processing device 130 may determine an intersection between the MRI image and the composite image of the total vertebrae. For example, based on spatial position information (e.g., position information and/or direction information) of a second MRI image in the cervical vertebra image segment, a first equation of a plane may be determined; based on spatial position information of the total vertebrae composite image, a second equation of a plane may be determined; and based on the first equation of the plane and the second equation of the plane, the processing device 130 may determine the intersection between the second MRI image in the cervical vertebra image segment and the total composite image. In some embodiments, based on the intersection, the processing device 130 may directly determine the first reference line on the composite image of the total vertebrae. In some embodiments, based on the intersection and a registration matrix, the processing device 130 may further adjust the position of the intersection, and determine a first intersecting line.

At 660, the processing device 130 may obtain a transformation matrix of the first reference line. In some embodiments, a user (e.g., a doctor) may manually adjust the position of the first reference line. The manual transformation may include translation, rotation, scale change, shear, etc., of the first reference line. A user (e.g., a doctor) may input a manual transformation command via an input/output component 760 in the computer 700. The processing device 130 may accept the manual transformation command, and effectuate the manual transformation of the position of the first reference line. In some embodiments, the manual transformation may also include deletion, addition, formatting, or the like, or a combination thereof, of the first reference line. For example, a doctor may input a manual transformation command via the input/output component 760, to delete one or more first reference lines. In some embodiments, the processing device 130 may automatically adjust the position of the first reference line based on user setting. For example, the processing device 130 may adjust the position of the first reference line on the composite image based on an objective function set by a user. In some embodiments, the processing device 130 may determine a transformation matrix based on transformation of the position of the first reference line. The transformation matrix may be a 4*4 matrix. The 4*4 matrix may be stored in the storage device 140 or in a cloud via the network 120.

At 670, the processing device 130 may update the position of the first reference line based on the transformation matrix, and may generate a second reference line. In some embodiments, a user may select whether or not to make a reference line update. For example, the user may select to update the first reference line via the input/output component 760, the processing device 130 may send a transformation matrix to the computer 700 or the mobile device 800; and based on the transformation matrix, the processing device 130 may update the position of the first reference line, and may generate the second reference line, the second reference line may display the position relationship between the MRI image and the composite image of the total vertebrae more precisely, so that a user (e.g., a doctor) may conveniently perform disease diagnosis and treatment.

Figure 7:
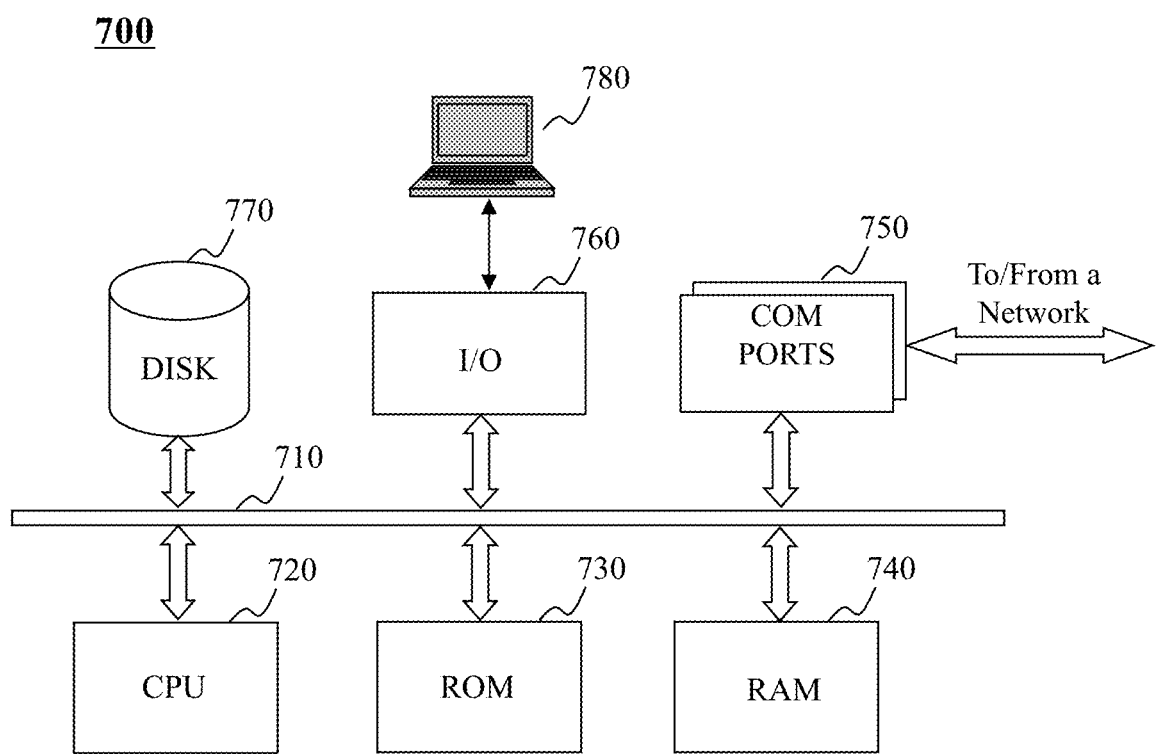
FIG. 7 illustrates an architecture of a computer device which may implement the system disclosed in the present disclosure according to some embodiments of the present disclosure.

FIG. 7 illustrates a structure of a computer device which may implement the system disclosed in the present disclosure according to some embodiments of the present disclosure. The system in the present embodiment may use a functional block diagram to explain a hardware platform containing a user interface. The computer may be a general-purpose computer or a specific-purpose computer. Both computers may be configured to implement the system in this embodiment. The computer 700 may be used to implement any components described currently which may offer information required by image integration. For example, the processing device 130 may be implemented by the computer such as a computer 700 through its hardware devices, software programs, firmware, or the like, or any combination thereof. For convenience, only one computer is depicted in FIG. 7, but the related computer functions described in this embodiment to provide the required information for the image integration may be implemented by a set of similar platforms in a distributed mode, which may decentralize a processing load of the system.

The computer 700 may include a communication port 750 that may be connected with a network to implement data communication. The computer 700 may also include a central processing unit (CPU) that may also include one or more processors to conduct program instructions. The exemplary computer platform may include an internal communication bus 710, a program storage unit in different forms, and a data storage unit. For example, a hard disk 770, a read only memory (ROM) 730, a random-access memory (RAM) 740, various data files that may be configured to be used for computer processing and/or communication, and possible program instructions executed by the CPU. The computer 700 may also include an input/output component 760 that supports input/output data streams between the computer and other components (e.g., the user interface 780). The computer 700 may also receive programs and data via a communication network.

Figure 8:
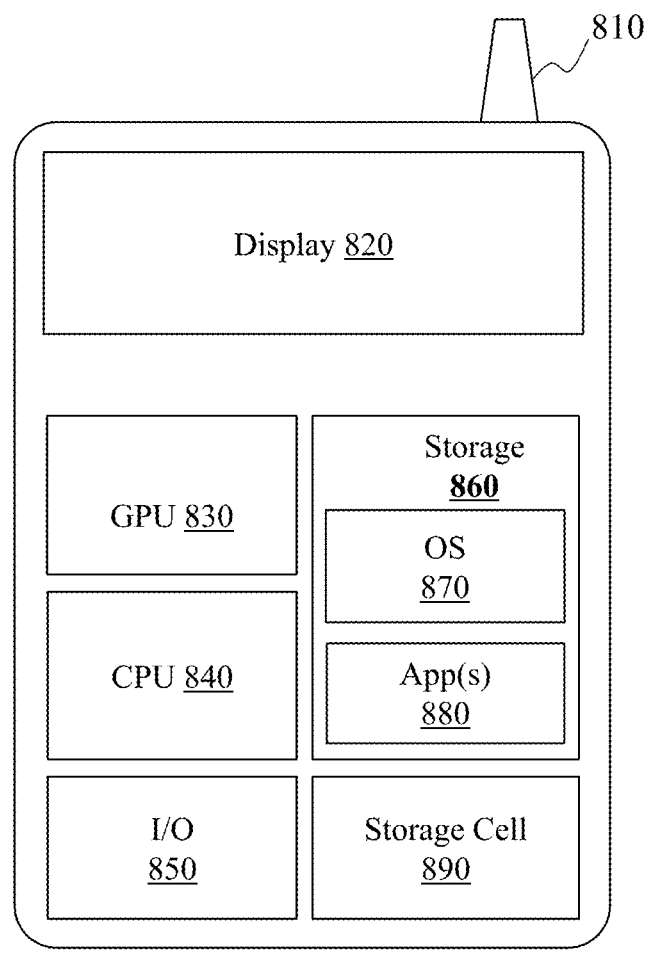
FIG. 8 illustrates a structure of a mobile device which may implement the system disclosed in the present disclosure according to some embodiments of the present disclosure; and, FIGS. 9-A to 9-C illustrate a schematic diagram of a result of precisely positioning of a reference line according to some embodiments of the present disclosure.

According to some embodiments of the present disclosure, FIG. 8 illustrates a structure of a mobile device which may implement the system disclosed in the present disclosure. In this embodiment, a mobile device 2800 for displaying and interacting with location-related information may include but is not limited to a smartphone, a tablet computer, a music player, a portable gaming machine, a global positioning system (GPS) receiver, a wearable computing device (e.g., eyeglasses, watches, etc.), or other forms that may be found in descriptions elsewhere of the present disclosure. The mobile device 800 in this embodiment may include one or more central processing units (CPUs) 840, graphical processing units (GPUs) 830, a display 820, a memory 860, an antenna 810 (e.g., a wireless communication unit), a storage unit 890, and one or more input/output (I/O) devices 850. Any other suitable components, the components may include but not limited to, system buses or controllers (not shown in the figure) may also be included in the mobile device 800. As shown in FIG. 8, a mobile operating system 870 (e.g. iOS, Android, Windows Phone, etc.) and one or more applications 880 may be loaded into the memory 860 from the storage unit 890 and may be executed by the central processing unit 840. The applications 880 may include a browser or other mobile applications that are suitable for receiving and processing information relating to the reference line on the mobile device 800. The information relating to the reference line with respect to users may be obtained by the input/output system devices 850 and may be provided to the processing device 130, and/or other components of the system 100, e.g., via the network 120.

In order to implement the different modules, units, and their functions as described in the previous disclosure, a computer hardware platform may be used as a hardware platform (e.g., the processing device 130, and/or other components of the system 100) for one or more of the elements described above. The hardware elements, operating systems, and programming languages of such computers are common in nature. It is assumed that those skilled in the art are familiar with these techniques and may use the techniques described herein to provide the required information for image integration. A computer containing user interface elements may be used as a personal computer (PC) or other types of workstations or terminal devices, and may also be used as servers after being properly programmed. It may be appreciated that those skilled in the art will be familiar with such structures, procedures, and general operations of such computer equipment, and therefore no additional explanation is required for all figures.

FIGS. 9-A through 9-C are schematic diagrams illustrating how to precisely position reference lines according to some embodiments of the present disclosure. FIG. 9-A is an axial image of a head; FIG. 9-B is a sagittal image of the head; and the FIG. 9-C is a coronal image of the head. In FIG. 9-A, 910 may be a reference line determined by the processing device 130 based on the axial image of the head and the coronal image of the head, and the reference line displays an intersecting line of the coronal image of the head (as shown in FIG. 9-C) on the axial image of the head. In FIG. 9-B, 920 may be a reference line determined by the processing device 130 based on the sagittal image of the head and the coronal image of the head, and the reference line displays an intersecting line of the head coronal image (as shown in FIG. 9-C) on the sagittal image of the head.

The above descriptions may disclose different aspects of methods for providing information required on image integration for implanting other operations by procedures. The procedures in the disclosure may be considered as "product" or "merchandise" existing in the form of executable codes and/or related data, which may be participated or implemented by a computer readable medium. A tangible and permanent storage medium may include any memory or storage used by a computer, a processor, a similar device, or a related module, for example, a semiconductor memory, a tape drive, a disk drive, or other devices that may provide storage functions for software at any time.

All software or a part of it may communicate over a network, such as the Internet or other communication networks. Such communications may load software from one computer device or processor to another. For example: from a management server or host computer in an imaging system loaded to a computer hardware platform, or other computer environment, or the similar function system relating to provide information required by the on-demand services. Thus, another medium that may deliver software elements may also be used as physical connections between local devices, such as light waves, radio waves, electromagnetic waves, etc., through cables, cables, or air. A physical medium used for a carrier, such as a cable, a wireless connection, or an optical cable, may also be considered a medium for carrying software. Here, unless the physical storage medium is restricted, other terms that may represent the computer or machine "readable medium" represent the medium in which a processor executes any instruction.

Therefore, a computer readable medium may have many forms, including, a visible storage media, a carrier media, or a physical transmission media. Stable storage media may include compact disks (CD), disks, or storage systems used in other computers or similar devices that may enable the system components described in the diagrams. Unstable storage media may include a dynamic memory, such as the main memory of a computer platform. The tangible transmission medium may include a coaxial cable, a copper cable, an optical fiber, and a circuitry forming the bus within the computer system. A carrier transmission medium may transmit electrical signals, electromagnetic signals, acoustic signals, or light wave signals, which may be generated by radio frequency or infrared data communication. A computer readable medium may include a hard disk, a floppy disk, a magnetic tape, any other magnetic medium; a CD-ROM, a DVD, a DVD-ROM, any other optical media; a hole punched card, and any other physical storage medium containing a hole patterns; a RAM, a PROM, an EPROM, a FLASH-EPROM, or any other memory chip tape; a carrier for data or instructions transmission, cable, a connection device for carrier transmission, or any other computer that may be used to read the code and/or data. In the form of these computer readable media, there are a variety of processes that occur when the processor is executing instructions and delivering one or more results.

The contents disclosed in this application can be diversified and improved. For example, different system components described above may be implemented by hardware, or software. For example, the system may be installed on the existing server. In addition, the location information disclosed here may be implemented through a firmware, a combination of firmware and software, a combination of firmware and hardware, or a combination of hardware, firmware and software.

The above descriptions may describe this application and/or some other examples. According to the above contents, the application may also make different variations. The topics disclosed in this application may be implemented in different forms and examples, and this application may be applied to a large number of applications. All the applications, modifications and changes required in the post claims are within the scope of this application.

What is claimed is:

1. A method for determining a reference line, comprising:
    obtaining at least two original images, the at least two original images corresponding to first spatial position information;
    determining a composite image based on the at least two original images, the composite image corresponding to second spatial position information;
    determining a composition relationship between the at least two original images; and
    determining at least one reference line based on the composition relationship between the at least two original images, the first spatial position information, and the second spatial position information, wherein the at least one reference line displays a positional relationship between one of the at least two original images and a reference image on the composite image, wherein the determining at least one reference line comprises:
        determining a first reference line based on the first spatial position information and the second spatial position information;
        obtaining, based on an objective function, a transformation matrix by performing at least one of translation or rotation operation to the first reference line; and
        obtaining a second reference line by correcting the first reference line based on the transformation matrix.

2. The method of claim 1, wherein the reference image includes the other one of the at least two original images or the composite image.

3. The method of claim 1, wherein the at least two original images include at least one of a CT image, an MRI image, or a PET image.

4. The method of claim 1, wherein the first spatial position information includes at least one of position information and direction information of the at least two original images; and the second spatial position information includes at least one of position information and direction information of the composite image.

5. The method of claim 1, wherein the determining a composition relationship between the at least two original images comprises performing at least one of operations to the at least two original images including:
translation;
rotation;
scale change; and
shear.

6. The method of claim 1, wherein the composition relationship between the at least two original images comprises a registration matrix.

7. The method of claim 1, wherein the determining at least one reference line based on the composition relationship between the at least two original images comprises:
determining an intersection between the at least two original images and the composite image based on the first spatial position information and the second spatial position information;
adjusting the intersection between the at least two original images and the composite image based on the composition relationship between the at least two original images; and
determining the at least one reference line based on the adjusted intersection between the at least two original images and the composite image.

8. The method of claim 7, wherein the determining the intersection between the at least two original images and the composite image based on the first spatial position information and the second spatial position information comprises:
determining the intersection based on at least one plane of the at least two original images and a plane of the composite image.

9. A reference line determination system comprises:
at least one storage medium including a set of instructions; and
at least one processor configured to communicate with the at least one storage medium, wherein when executing the set of instructions, the at least one processor is configured to direct the system to perform operations including:
obtaining at least two original images, said at least two original images corresponding to first spatial position information;
determining a composite image based on the at least two original images, the composite image corresponding to second spatial position information;
determining a composition relationship between the at least two original images; and
determining at least one reference line based on the composition relationship between the at least two original images, the first spatial position information, and the second spatial position information, wherein the at least one reference line displays a positional relationship between one of the at least two original images and a reference image on the composite image, wherein the determining at least one reference line comprises:
determining a first reference line based on the first spatial position information and the second spatial position information;
obtaining, based on an objective function, a transformation matrix by performing at least one of translation and rotation operation to the first reference line; and
obtaining a second reference line by correcting the first reference line based on the transformation matrix.

10. The reference line determination system of claim 9, wherein the reference image includes the other one of the at least two original images or the composite image.

11. The reference line determination system of claim 9, wherein the at least two original images include at least one of a CT image, an MRI image, or a PET image.

12. The reference line determination system of claim 9, wherein the first spatial position information includes at least one of position information and direction information of the at least two original images; and the second spatial position information includes at least one of position information or direction information of the composite image.

13. The reference line determination system of claim 9, wherein the determining a composition relationship between the at least two original images comprises performing at least one of operations to the at least two original images including:
translation;
rotation;
scale change; and
shear.

14. The reference line determination system of claim 9, wherein the composition relationship between the at least two original images comprises a registration matrix.

15. The reference line determination system of claim 9, wherein the determining at least one reference line based on the composition relationship between the at least two original images comprises:
determining an intersection between the at least two original images and the composite image based on the first spatial position information and the second spatial position information;
adjusting the intersection between the at least two original images and the composite image based on the composition relationship between the at least two original images; and
determining the at least one reference line based on the adjusted intersection between the at least two original images and the composite image.

16. The reference line determination system of claim 15, wherein the determining the intersection between the at least two original images and the composite image based on the first spatial position information and the second spatial position information comprises:
determining the intersection based on at least one plane of the at least two original images and a plane of the composite image.

17. A non-transitory readable medium, comprising at least one set of instructions, wherein when executed by at least one processor of a computing device, the at least one set of instructions directs the at least one processor to perform a method, the method comprising:
obtaining at least two original images, the at least two original images corresponding to first spatial position information;
determining a composite image based on the at least two original images, the composite image corresponding to second spatial position information;
determining a composition relationship between the at least two original images; and determining at least one reference line based on the composition relationship between the at least two original images, the first spatial position information, and the second spatial position information, wherein the at least one reference line displays a positional relationship between one of the at least two original images and a reference image on the composite image, wherein the determining at least one reference line comprises:

determining a first reference line based on the first spatial position information and the second spatial position information;

obtaining, based on an objective function, a transformation matrix by performing at least one of translation and rotation operation to the first reference line; and obtaining a second reference line by correcting the first reference line based on the transformation matrix.

18. The non-transitory readable medium of claim 17, wherein the reference image includes the other one of the at least two original images or the composite image.

* * * * *